United States Patent [19]

DeGraw et al.

[11] 4,218,454

[45] Aug. 19, 1980

[54] N-αMETHYLCYCLOPROPYLMETHYL DERIVATIVES OF NORMORPHINE AND NOROODEINE, AND ANALGESIC COMPOSITIONS AND METHODS EMPLOYING THE NORMORPHINE DERIVATIVES

[75] Inventors: Joseph I. DeGraw, Sunnyvale; John A. Lawson, Monte Vista; Howard L. Johnson, Sunnyvale; Gilda H. Loew, Atherton, Calif.; Donald A. Berkowitz, El Cerrito, all of

[73] Assignee: SRI International, Menlo Park, Calif.

[21] Appl. No.: 909,257

[22] Filed: May 24, 1978

Related U.S. Application Data

[63] Continuation-in-part of Ser. No. 813,796, Jul. 8, 1977, abandoned.

[51] Int. Cl.$^2$ .................. A61K 31/485; C07D 489/02
[52] U.S. Cl. ........................................ 424/260; 546/44
[58] Field of Search ...................... 260/285; 424/260; 544/44

[56] References Cited

U.S. PATENT DOCUMENTS

| | | | |
|---|---|---|---|
| 2,741,609 | 4/1956 | Weijlard | 260/285 |
| 2,741,614 | 4/1956 | Clark | 260/285 |
| 3,393,197 | 7/1968 | Pachter et al. | 546/44 |
| 3,468,891 | 9/1969 | Bartels-Keith et al. | 424/260 X |
| 3,676,557 | 7/1972 | Lachman et al. | 424/260 |

OTHER PUBLICATIONS

Clark et al., J. Am. Chem. Soc., vol. 75, pp. 4963–4966 (1953).
Winter et al., Arch. Int. Pharmacodyn. CX No. 2–3, pp. 186–202 (1957).
Loew et al., Opiates Endog. Opiod. Pept. Proc. Int. Narc. Res. Club Meet. 1976, 399–402, Abstract CA V. 87, 127012g.

*Primary Examiner*—Donald G. Daus
*Assistant Examiner*—Diana G. Rivers
*Attorney, Agent, or Firm*—Donovan J. DeWitt

[57] ABSTRACT

Novel N-sec-alkyl derivatives of norcodeine and normorphine wherein the sec-alkyl group contains either four or five carbon atoms. Specifically included are those derivatives of norcodeine and normorphine wherein the sec-alkyl group is 2-butyl, 3-pentyl, α-methylallyl and α-methylcyclopropylmethyl. The normorphine derivatives have strong agonist potency combined with strong antagonist qualities and indicated low addiction potential. The norcodeine analogs are useful as intermediates in preparing the corresponding normorphine compounds.

5 Claims, No Drawings

N-αMETHYLCYCLOPROPYLMETHYL DERIVATIVES OF NORMORPHINE AND NOROODEINE, AND ANALGESIC COMPOSITIONS AND METHODS EMPLOYING THE NORMORPHINE DERIVATIVES

The invention described herein was made in the course of work under a grant or award from the Department of Health, Education and Welfare.

This application is a continuation-in-part of Ser. No. 813,796, filed July 8, 1977, now abandoned.

BACKGROUND OF INVENTION

It is an object of this invention to provide novel compounds having potent analgesic properties similar to morphine, but with only slight addiction potential similar to the potent narcotic antagonist, N-allylnormorphine (Nalline).

Many N-alkyl analogs of norcodeine and normorphine are known, see, for example, R. L. Clark, A. A. Pessolano, J. Weijlard and K. Pfister, 3rd, Am. Chem. Soc. J., 75, 4963–4966, (1953).

Previous exploration has concerned the N-primary alkyl analogs of norcodeine and normorphine. These N-alkyl analogs have not found clinical acceptance either because they lack the required potency or were considered to have excessive potential for addiction liability.

It has been taught in the work of Archer, et al., J. Med. Chem., 7, 123–127 (1964) that compounds possessing potent analgesic properties along with a degree of antagonist activity are useful analgesics in the clinic, usually having far less addiction potential than pure agonist compounds. Such an example is the clinically useful drug, pentazocine, a dual agonist-antagonist with an analgesic potency about one-fourth that of morphine.

The present invention provides novel N-sec-alkyl analogs of norcodeine and normorphine which have potent analgesic and antagonist qualities. The only known N-sec-alkyl norcodeine and normorphine analogs are the N-isopropyl-norcodeine and N-isopropyl-normorphine compounds which are taught in the Clark et al. paper. However, as reported by co-workers of Clark et al. who performed the pharmacological testing, the N-isopropyl-normorphine compound was not a good agonist and had little, if any, antagonist qualities. The N-isopropyl-norcodeine was, of course, inactive. See Charles A. Winter, Peter D. Orahovats and Edward G. Lehman, Arch. Int. Pharmcodyn, CX, No. 2–3, 186–202, (1957).

While some N-alkylnormorphines (such as N-butyl-, N-amyl-, or N-hexylnormorphine) have potent analgesic activity, they are devoid of antagonist properties. See Clark et al. paper. On the other hand, N-primary loweralkyl normorphines such as N-propyl normorphine and N-isobutylnormorphine have been shown to be morphine antagonists only. See U.S. Pat. No. 2,741,609 to John Weijlard and U.S. Pat. No. 2,741,614 to Robert L. Clark, as well as the data presented herein for N-propylnormorphine.

We have found that N-2-butyl, N-3-pentyl, N-α-methylallyl and N-α-methylcyclopropylmethyl derivatives of normorphine, together with the acid salts thereof possess analgesic activities similar to morphine while at the same time displaying antagonist properties indicative of low addiction potential. These results are particularly surprising in view of the fact that other N-lower alkylnormorphines do not demonstrate this mixed agonist-antagonist activity with the expected useful range of analgesic potency.

SUMMARY OF INVENTION

This invention is based on the discovery of certain novel N-sec-alkyl analogs of norcodeine and normorphine wherein the sec-alkyl group is selected from the group consisting of 2-butyl, α-methylallyl, 3-pentyl and α-methylcyclopropylmethyl. The particular compounds falling within this group to which claim is made include:

| COMPOUND | COMPOUND NO. |
| --- | --- |
| N-2-butylnorcodeine | 3,3(R),3(S) |
| N-α-methylallylnorcodeine | 4,4(R) |
| N-α-methylcyclopropylmethylnorcodeine | 5 |
| N-3-pentylnorcodeine | 6 |
| N-2-butylnormorphine | 7,7(R),7(S) |
| N-α-methylallylnormorphine | 8(R) |
| N-α-methylcyclopropylmethylnormorphine | 9 |
| N-3-pentylnormorphine | 10 |

In the above listing of compound numbers (R) refers to the compound as present in the (R) diastereomeric form, while (S) similarly represents the compound as present in the (S) diastereomeric form. The compound number standing without the (R) and (S) indicia (compound numbers 3, 4, 5, 7, 8 and 9) represent mixtures of the indicated (R) and (S) diastereomerics. Further, it may be noted that the normorphine compounds enumerated above were recovered in their HCl salt forms, as more fully discussed below.

The compounds of the present invention are those having the structure:

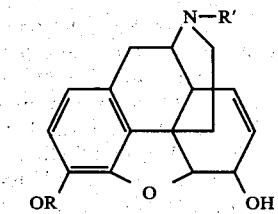

wherein R and R' may represent the groups enumerated below, those wherein R represents methyl being norcodeine derivatives while those where R is hydrogen are normorphine derivatives.

| Compound No. | R | R' |
| --- | --- | --- |
| 3 | CH₃ | —CH(CH₃)CH₂CH₃ (2-butyl) |
| 4 | CH₃ | —CH(CH₃)CH=CH₂ (α-methylallyl) |
| 5 | CH₃ | —CH(CH₃)—◁ (α-methylcyclopropylmethyl) |
| 6 | CH₃ | —CH(CH₂CH₃)₂ (3-pentyl) |
| 7 | H | —CH(CH₃)CH₂CH₃ (2-butyl) |
| 8 | H | —CH(CH₃)CH=CH₂ (α-methylallyl) |
| 9 | H | —CH(CH₃)—◁ (α-methylcyclopropylmethyl) |
| 10 | H | —CH(CH₂CH₃)₂ (3-pentyl) |

The compounds having the (S) diastereomeric form have the configuration

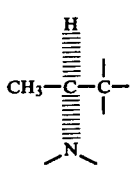

S-configuration while those with the R configuration have the structure

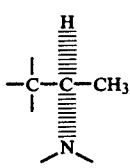

R - configuration

The N-sec-alkylnormorphine compounds of the present invention have utility as potent analgesics when administered to warm-blooded animals, they also having strong antagonistic qualities and an indicated low addition potential.

The corresponding N-sec-alkylnorcodeine analogs have utility as precursor intermediates for use in preparing the corresponding normorphine compounds.

There follow examples disclosing one or more methods for the preparation of each of the compounds of the present invention which are enumerated above:

EXAMPLE I

N-2-butylnorcodeine 3 (Method A)

A mixture of 39 g (0.137 mole) of norcodeine 1 19.5 g (0.274 mole) of lactonitrile, and 18 ml of toluene was stirred with gentle warming until the mixture became homogeneous. Then, the solvent was removed in vacuo to leave a crystalline residue (47 g, 100%) of N-α-cyano-ethyl-norcodeine 2. Without further purification, 21 g (0.062 mole) of the lactonitrile adduct 2 was dissolved in 500 ml of dried tetrahydrofuran and the solution treated with 0.15 mole of ethyl magnesium bromide in 500 ml of diethyl ether with vigorous stirring. After 15 minutes the resulting mixture was poured over ice, and the organic phase separated, dried over magnesium sulfate, and evaporated in vacuo to give 15.4 g (73%) of N-2-butylnorcodeine 3 as a gum. The proton NMR spectrum was in agreement with that expected for 3.

N-2-butyl-norcodeine (Method B) (3 (R) and 3 (S) forms)

A mixture of 8.5 g (0.056 mole) of R(−)-2-mesyloxybutane (the methanesulfonic acid ester of (R)-2-butanol), 3.2 g (0.011 mole) of 1, and 8.0 g (0.075 mole) of Na₂CO₃ was stirred without solvent at 75° C. for 16 hours. Then, the reaction mixture was poured into water-chloroform, and the chloroform layer separated and extracted with 100 ml of 3 N hydrochloric acid. The combined aqueous layers were basified to pH 8-9 with 3 N ammonium hydroxide, and the gummy precipitate extracted into 150 ml of dichloromethane. The organic layer was separated, dried over magnesium sulfate, decolorized over Norite, filtered and evaporated to yield 1.15 g (31%) of N-(S)-2-butyl-norcodeine 3(S) as a gum. By an identical procedure, the (R) diastereomer of 3 was prepared in 30% yield by the reaction of norcodeine 1 with S(+)-2-mesyloxy butane. ¹³C-NMR spectroscopy served to differentiate the diastereomers and showed the separately prepared diastereomers (3 (R) and 3 (S)) to contain less than 5% of the opposite epimer.

EXAMPLE II

N-α-methylallylnorcodeine 4

Analogous to the preparation of 3 (Method A), 4 is produced by the addition of 0.13 mole of vinyl magnesium bromide in 500 ml of tetrahydrofuran to a solution of 17.5 g (0.052 mole) of the lactonitrile adduct 2 in 500 ml of tetrahydrofuran. The yield was 15 g (85%) of crude product, after a similar work up as described for 3. The proton NMR spectrum of the gum so obtained was in agreement with that expected for 4.

EXAMPLE III

N-α-methylcyclopropylmethylnorcodiene 5

Analogous to the preparation of 3 (Method A), 5 is produced by the addition of 0.20 mole of cyclopropyl magnesium bromide in 300 ml of tetrahydrofuran to a solution of 20 g (0.06 mole) of the lactonitrile adduct 2 in 75 ml of tetrahydrofuran. The reaction was worked up in a manner analogous to that described for 3 to yield 24.7 g. The proton NMR spectrum of the gum so obtained was in agreement with that expected for 5.

EXAMPLE IV

N-3-pentylnorcodeine 6

A mixture of 11.0 g (0.073 mole) of 3-bromopentane, 2.0 g (0.007 mole) of 1 and 7 g (0.066 mole) of sodium carbonate and 6 ml of dimethylformamide after stirring for 20 hours at 120° C., yielded 3.0 g of a crude gum. Following chromatography on silica gel, 0.75 g (30%) of the desired product 6 was obtained. The proton NMR spectrum was in agreement with that expected for 6.

EXAMPLE V

N-2-butylnormorphine.Hydrochloride (7, R and S forms)

A solution of 25.0 g (0.073 mole) of 3 (mixture of R and S epimers from Method A) in 500 ml of dry tetrahydrofuran was treated with 18.6 g (0.10 mole) of diphenylphosphine and cooled to 0° C. Then 140 ml of 1.6 N butyl lithium in hexane was added rapidly by syringe. The mixture was allowed to warm to room temperature and was then heated to gentle reflux for 30 minutes. The reaction was quenched by slow addition of 100 ml of 2 N hydrochloric acid. The solvents were evaporated in vacuo and the aqueous residue washed thrice with 200-ml portions of ether. The aqueous layer was made strongly alkaline with 10% sodium hydroxide, and washed again with 200 ml of diethyl ether. The pH was adjusted to pH 8-9 and the aqueous mixture extracted with 400 ml of dichloromethane. The organic layer was separated, dried, filtered and evaporated to yield 24 g of a foamy residue. This material was dissolved in 500 ml of isopropanol and treated with 95 ml of 3% methanolic hydrogen chloride solution. Evaporation of the bulk of the isopropanol and dilution with ether resulted in precipitation of 24.5 g (89%) of white crystals containing the (R) and (S) isomers of 7 in a 3:7 ratio as shown by $^{13}$C-NMR. Recrystallization from isopropanol afforded 15.5 g (56%) of the hydrochloride of the S-epimer 7 (S), m.p. 338° (dec.); $[\alpha]_D^{21°}$ −112° (CH$_3$OH). Calc'd. (C$_{20}$H$_{25}$NO$_3$.HCl): C, 66.02; H, 7.15; N, 3.85. Found: C, 65.77; H, 7.13; N, 3.79. Concentration of the mother liquor from preparation of 7 (S) and further crystallization afforded 0.45 g (1.6%) of the hydrochloride of the R-diastereomer, 7 (R), m.p. 213°–15° (dec.); $[\alpha]_D^{21°}$ −102° (CH$_3$OH). Calc'd. (C$_{20}$H$_{25}$NO$_3$.HCl): C, 66.02; H, 7.15; N, 3.85. Found: C, 65.74; H, 7.05; N, 3.60. The separately prepared diastereomers (3 R and 3 S, Method B) were each demethylated to 7 (R) and 7 (S), respectively. Physical properties of the hydrochlorides were in agreement with those reported above.

EXAMPLE VI

N-α-methylallylnormorphine.Hydrochloride 8 (R)

In a manner analogous to the preparation of 7 8.0 g (0.23 mole) of N-α-methylallylnorcodeine (4, mixture of R and S Forms) was treated with 7 g of diphenylphosphine and 60 ml of 1.6 N butyl lithium in hexane. The crude product, as the free base, was crystallized from ethyl acetate/ether (3.60 g) and contained 60% of material regarded as the R-isomer and 40% of the S-isomer as shown by $^{13}$C-NMR. Preparation and recrystallization of the crude hydrochloride salt from methanol/isopropanol afforded 1.75 g (21%) of 8 (R), m.p. 303°–4° C.; $[\alpha]_D^{21°}$ −120° (MeOH); calc'd. (C$_{20}$H$_{23}$NO$_3$.HCl); C, 66.39; H, 6.64; N, 3.87. Found: C, 66.14, H, 6.72; N, 3.79.

EXAMPLE VII

N-α-methylcyclopropylmethylnormorphine.Hydrochloride 9

Treatment of 24.7 g of N-α-methylcyclopropylmethylnorcodeine (5) with 25 g of diphenylphosphine and 135 ml of 1.4 N butyl lithium in hexane according to the previous example afforded 10.7 g of crude free base. The material was chromatographed on silica gel (600 g) to give 8.0 g (40%) of pure base. The hydrochloride salt was prepared in and crystallized from methanol/n-octanol, mp 248°–250°. Calc'd (C$_{21}$H$_{25}$NO$_3$.HCl.H$_2$O); C, 64.0; H, 7.12; N, 3.56. Found: C, 64.3; H, 6.99; N, 3.46.

EXAMPLE VIII

N-3-pentylnormorphine.Hydrochloride 10

Treatment of 0.70 g of N-3-pentylnorcodeine 6 with 0.8 g of diphenylphosphine and 7.0 ml of 1.6 N butyl lithium in hexane according to the previous example afforded 0.63 g of crude 10 as the hydrochloride salt. Recyrstallization from isopropanol gave 0.28 g (38%) of 10, m.p. 295° C. (dec.). Calc'd. (C$_{21}$H$_{27}$NO$_3$.HCl): C, 66.7; H, 7.47; N, 3.71. Found: C, 66.6; H, 7.57; N, 3.61.

It will be noted that the N-sec-alkyl normorphines recited above are prepared in the form of an acid salt. These acid addition salts (shown as those of HCl) are preferably the pharmaceutically accepted, nontoxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic acids, and organic sulphonic acids, for example, methanesulphonic and toluene-p-sulphonic acids. These normorphine derivative compounds are preferably employed in the salt form since they then have adequate solubility in water. However, they can be employed in the nonacid condition.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide, with a metal carbonate, such as an alkali metal or an alkaline earth metal carbonate or hydrogen carbonate, for example sodium, potassium or calcium carbonate or hydrogen carbonate; with ammonia, or with a hydroxyl ion exchange resin, or with any other suitable reagent. An acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

The compounds of this invention or the salts thereof can be administered to animals by an available route, including oral and parenteral (intravenous, intraperitoneal, subcutaneous, and intramuscular) administration.

BIOLOGICAL TESTS

Using mice, the compounds of this invention were subjected to the Tail Flick Analgesic Assay, the Writhing Analgesic Assay, the Straub Tail Antagonist Assay and the Mouse Jump Physical Dependence Assay, said assays being described in the literature as follows:

Tail Flick Analgesic Assay
  D'Amour, F. E and Smith, D. L., J. Pharmacol. Exp. Therap. 72, 74–79 (1941)
  Howes, J. F., Harris, L. S., Dewey, W. L. and Voyda, C. A., J. Pharmacol. Exp. Therap. 169, 23–28 (1969)
  Dewey, W. L., Harris, L. S., Howes, J. F. and Nuite, J. A., J. Pharmacol. Exp. Therap. 175, 435–442 (1970)

Writhing Analgesic Assay
  Blumberg H., Wolf, P. S. and Dayton, H. B., Proc. Soc. Exper. Biol. Med., 118, 763 (1965).

Straub Tail Antagonist Assay
  Blumberg, H. and Dayton, H. B. In Narcotic antagonists Advances in Biochemical Psychopharmacology, Vol. 8, Ed., Brande, M. C., Harris L. S.

Mouse Jump Test
  Saelens, J. K., Granat, F. R. and Sawyer, W. K. Arch. int. Pharmacodyn 190, 213–218 (1971).

The Tail Flick Analgesic Assay represents a test procedure in which heat from an intense light source is focused on the mouse's tail. When pain is detected by the mouse the tail gives a characteristic flicking response. In untreated controls the intervals from exposure to flick is about 2 seconds, while when using an effective analgesic the interval from exposure to flick is usually about 6 to 10 seconds. The ED$_{50}$ values given in Table 1 below represent the dose [micromoles (μM) per kg of body weight] which gives a group means response time of 5 seconds.

The Writhing Analgesic Assay test is one in which mice injected i.p. with a solution of phenylquinone exhibit a typical writhing response. The ED$_{50}$ values given in Table 1 below represent the dose ($\mu$M/kg) which eliminates any such writhing in 50% of the treated mice.

Table 1

Relative Analgesic Activity

| Compound No. | Tail Flick (ED$_{50}$, $\mu$M/kg) | Writhing (ED$_{50}$, $\mu$M/kg) |
|---|---|---|
| Morphine | 10.5 | 1.5 |
| 7(S) | 13.4 | 11.0 |
| 7(R) | 19.0 | 6.4 |
| 8(R) | 44.5 | 13.0 |
| 9 | 12.4 | 0.69 |
| 10 | 19.9 | 2.3 |

The Straub Tail Antagonist Assay is one in which mice injected with morphine exhibit a characteristic positioning of the tail commonly known as the "Straub tail". The ED$_{50}$ values given in Table 2 below represent that dose which abolishes this response in 50% of the test mice.

Table 2

Relative Antagonist Activity

| Compound No. | Inhibition of Straub tail response (ED$_{50}$, $\mu$M/kg) |
|---|---|
| Morphine | No inhibition |
| Nalorphine | 1.0 |
| 7(S) | 7.4 |
| 7(R) | 16.2 |
| 8(R) | 11.0 |
| 9 | 4.5 |
| 10 | 17.2 |

Using mice, tests were made to determine the physical dependence capacity of compounds 7 (S) 7 (R) and 9 as measured by the Mouse Jump Test, this being a simple screening method to estimate the physical dependence capacity of analgesics. In this mouse jumping test, the mice are injected (i.p.) 5× on day 1 with gradually increasing dosages ranging from 8 to 100 mg/kg of body weight. On days 2 and 3 the mice (in all except one test) were given 100 mg/kg 4×. In the one test, dosage was raised to 200–300 mg/kg on day 2 and to 300 mg/kg on day 3. On day 4 all the mice received one shot (100 mg/kg) of the antagonist Naloxone. Following this all mice were caged for 30 minutes and a record was made of the number of mice jumping during this interval. The results obtained are expressed in the following Table 3, it being noted that when using morphine all of the mice showed withdrawal symptoms as evidenced by their jumping, while with compounds 7 (S) 7 (R) and 9 as well as with Nalline, the number of mice jumping was very small:

Table 3

Physical Dependence Capacity of 2-Butylnormorphine . HCl and N-α-methylcyclopropylmethylnormorphine . HCl as measured by Mouse Jump Test

| Compound No. | Dose (mg/kg) Day 1 | Day 2 | Day 3 | Day 4 | Total Number Mice Tested | Total Number Mice Affected (Jumped) |
|---|---|---|---|---|---|---|
| 7(S) | 8–100 | 100 | 100 | * | 20 | 2 |
| 7(S) | 8–100 | 200–300 | 300 | * | 10 | 1 |
| 7(R) | 8–100 | 100 | 100 | * | 12 | 1 |
| 9 | 8–100 | 100 | 100 | * | 10 | 1 |
| Morphine | 8–100 | 100 | 100 | * | 10 | 10 |
| Nalline | 8–100 | 100 | 100 | * | 12 | 0–3 |

Table 3-continued

Physical Dependence Capacity of 2-Butylnormorphine . HCl and N-α-methylcyclopropylmethylnormorphine . HCl as measured by Mouse Jump Test

| Compound No. | Dose (mg/kg) Day 1 | Day 2 | Day 3 | Day 4 | Total Number Mice Tested | Total Number Mice Affected (Jumped) |
|---|---|---|---|---|---|---|
| Saline | — | — | — | * | 15 | 0 |

*received 100 mg/kg Naloxone

The compounds used in a practice of this invention, including any salts thereof, have good antagonist characteristics and can be administered to the warm-blooded animal by any available route, including oral and parenteral (intravenous, intraperitoneal, subcutaneous and intramuscular) administration, with substantially little addiction potential. The amount administered is sufficient to ameliorate pain and generally to provide the desired degree of analgesia, said amount depending upon the species of animal, and the weight of the animal. For example, in human administration, a dosage of a compound of the present invention within the range from about 2 to 1750 mg per day should be sufficient to provide the desired degree of analgesia. The upper limit dosage is that imposed by toxic side effects, and can be determined by trial and error for the species of animal to be treated.

To facilitate administration, the compounds employed in a practice of this invention, including the salts thereof, can be provided in composition form, and preferably in dosage unit form. While any compound selected can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic. The carrier or diluent can be solid, semisolid, or liquid, and can serve as a vehicle, excipient, or medium for the active agent. Exemplary diluents and carriers include sterile water, lactose, dextrose, sucrose, sorbitol, mannitol, starches, gum acacia, calcium, phosphate, mineral oil, cocoa butter, oil of theobroma, alginates, tragacanth, gelatin, syrup, methyl cellulose, polyoxyethylene sorbitan, monolaurate, methyl- and propyl-hydroxybenzoate, talc or magnesium stearate.

For convenience in handling, the compounds employed in a practice of this invention and the carrier or diluent can be enclosed or encapsulated in a capsule, sachet, cachet, gelatin, paper or other container, especially when intended for use in dosage units. The dosage units can for example take the form of tablets, capsules, suppositories or cachets.

The following examples illustrate various form of dosage units in which compound 7 (R and/or S) can be prepared, said compound being typical of the other compounds which can be employed in a practice of this invention:

EXAMPLE IX

| Tablet formulation | Mg/tablet |
|---|---|
| N-2-butylnormorphine . HCl 7 | 100 |
| Lactose | 86 |
| Cornstarch (dried) | 45.5 |

| Tablet formulation | |
|---|---|
| | Mg/tablet |
| Gelatin | 2.5 |
| Magnesium stearate | 1.0 |

Compound 7 is powdered and passed through a mesh sieve and well mixed with the lactose and 30 mg of the cornstarch, both passed through a sieve. The mixed powders are massed with a warm gelatin solution, prepared by stirring the gelatin in water and heating to form a 10% w/w solution. The mass is granulated by passing through a sieve, and the moist granules dried at 40° C. The dried granules are regranulated by passing through a sieve and the balance of the starch and the magnesium stearate is added and thoroughly mixed.

EXAMPLE X

| Capsule formulation | |
|---|---|
| | Mg/capsule |
| Compound 7 | 200 |
| Lactose | 150 |

Compound 7 and lactose are passed through a sieve and the powders well mixed together before filling into hard gelatin capsules of suitable size, so that each capsule contains 350 mg of mixed powders.

EXAMPLE XI

| Suppositories | |
|---|---|
| | Mg/suppository |
| Compound 7 | 50 |
| Oil of theobroma | 950 |

Compound 7 is powdered and passed through a sieve and triturated with molten oil of theobroma at 45° C. to form a smooth suspension. The mixture is well stirred and poured into molds, each of nominal 1 g capacity, to produce suppositories.

EXAMPLE XII

| Cachets | |
|---|---|
| | Mg/cachet |
| Compound 7 | 100 |
| Lactose | 400 |

Compound 7 is passed through a mesh sieve, mixed with lactose previously sieved and fitted into cachets of suitable size so that each contains 500 mg.

EXAMPLE XIII

| Intramuscular injection (sterile suspension in aqueous vehicle) | |
|---|---|
| | Mg |
| Compound 7 | 10 |
| Sodium citrate | 5.7 |
| Sodium carboxymetylcellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE XIV

| Intraperitoneal intraveneous or subcutaneous injection (sterile solution in aqueous carrier system) | |
|---|---|
| | Mg |
| Compound 7 | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

The present invention forms the subject of the following paper: Analgesics. 1. Synthesis and Analgesic Properties of N-sec-alkyl and N-tert-alkylnormorphines, J. I. De Graw, J. A. Lawson, J. L. Crase, H. L. Johnson, M. Ellis, E. T. Uyeno, G. H. Loew and D. S. Berkowitz, J. Med. Chem. 21, 415–422 (1978).

We claim:

1. Compounds having the structure

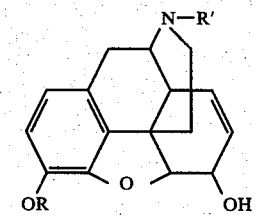

wherein R represents hydrogen or methyl and wherein R' represents α-methylcyclopropylmethyl, together with their pharmaceutically acceptable acid addition salts.

2. The compound of claim 1 which is N-α-methylcyclopropylmethylnorcodeine.

3. The compound of claim 1 which is N-α-methylcyclopropylmethylnormorphine.

4. A dosage unit for pharmaceutical composition for the amelioration of pain comprising an amount within a range of from about 2 to 1750 mg per dosage unit, therapeutically effective to ameliorate pain, N-α-methylcyclopropylmethylnormorphine, and its pharmaceutically acceptable acid addition salts, together with a pharmaceutically acceptable nontoxic carrier or diluent therefor.

5. A method having little addiction potential for ameliorating pain in a warm-blooded animal, said method comprising administering to said animal an amount, effective to ameliorate the pain, of N-α-methylcyclopropylmethylnormorphine together with the pharmaceutically acceptable acid addition salts thereof, said compounds having good antagonist characteristics.

* * * * *

UNITED STATES PATENT AND TRADEMARK OFFICE
CERTIFICATE OF CORRECTION

PATENT NO. : 4,218,454
DATED : Aug. 19, 1980
INVENTOR(S) : Joseph I. De Graw, et al.

It is certified that error appears in the above-identified patent and that said Letters Patent are hereby corrected as shown below:

In the title page: in the title, line 3, change

"NOROODEINE" to "NORCODEINE"

Column 1, line 3, change "NOROODEINE" to "NORCODEINE"

Signed and Sealed this

Twenty-sixth Day of January 1982

[SEAL]

Attest:

Attesting Officer

GERALD J. MOSSINGHOFF

Commissioner of Patents and Trademarks